Figure 1:
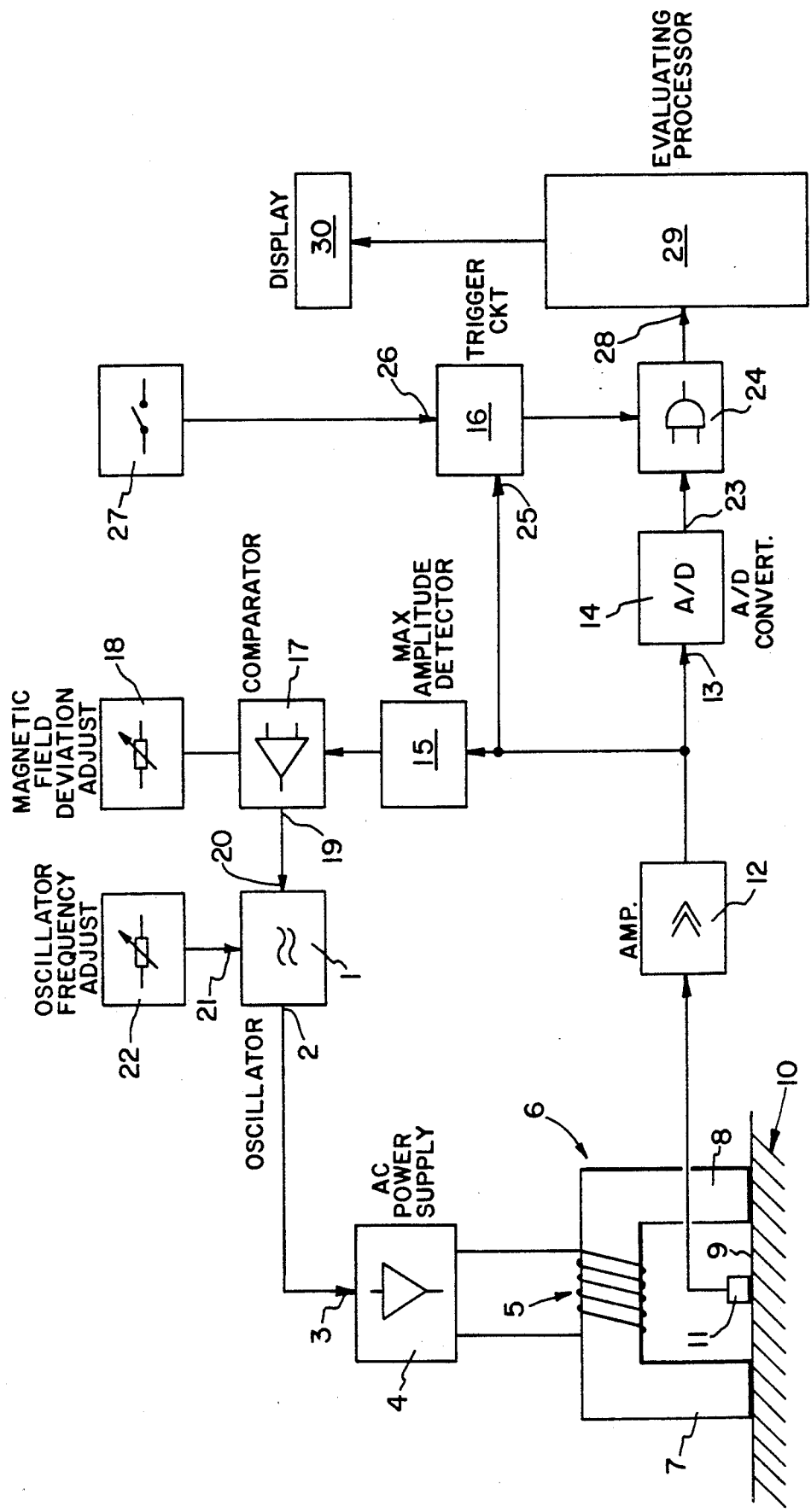

United States Patent [19]

Dobmann et al.

[11] Patent Number: 5,028,869
[45] Date of Patent: Jul. 2, 1991

[54] PROCESS AND APPARATUS FOR THE NONDESTRUCTIVE MEASURING OF MAGNETIC PROPERTIES OF A TEST BODY, BY DETECTING A TANGENTIAL MAGNETIC FIELD AND DERIVING HARMONIC COMPONENTS THEREOF

[75] Inventors: Gerd Dobmann, Dudweiler; Holger Pitsch, Saarbrucken, both of Fed. Rep. of Germany

[73] Assignee: Fraunhofer-Gesellschaft Zur Forderung der Angewandten Forshung E.V., Munich, Fed. Rep. of Germany

[21] Appl. No.: 445,694
[22] PCT Filed: Mar. 17, 1989
[86] PCT No.: PCT/DE89/00172
§ 371 Date: Nov. 27, 1989
§ 102(e) Date: Nov. 27, 1989
[87] PCT Pub. No.: WO89/10557
PCT Pub. Date: Nov. 2, 1989

[30] Foreign Application Priority Data

Apr. 23, 1988 [DE] Fed. Rep. of Germany ....... 3813739

[51] Int. Cl.$^5$ .................. G01N 27/72; G01N 27/80; G01R 33/14
[52] U.S. Cl. .................................... 324/223; 324/235
[58] Field of Search ............... 324/209, 222, 223, 227, 324/235, 239

[56] References Cited

U.S. PATENT DOCUMENTS

| | | | |
|---|---|---|---|
| 3,636,437 | 1/1972 | Soulant, Jr. et al. | 324/209 |
| 4,623,841 | 11/1986 | Stinson et al. | 324/223 |
| 4,881,030 | 11/1989 | Stuecker et al. | 324/209 |

FOREIGN PATENT DOCUMENTS

| | | |
|---|---|---|
| 3037932 | 4/1982 | Fed. Rep. of Germany . |
| 2312777 | 5/1975 | France . |
| 8700293 | 1/1987 | PCT Int'l Appl. . |
| 819684 | 4/1981 | U.S.S.R. ............... 324/239 |

OTHER PUBLICATIONS

"Hardness Inspection of 38KhA14 Steel Parts by the Electromagnetic Method With Higher Harmonica", 2422 Industrial Laboratory, Feb. 1977, pp. 264-266.
"Effects of Grain Size, Hardness and Stress on the Magnetic Hysteresis Loops of Ferromagnetic Steels", Journal of Applied Physics, Feb. 15, 1987 pp. 1576-1579.
"Nondestructive Measurement of Stress In Ferromagnetic Steels Using Harmonic Analysis of Induced Voltage", NDT International, Jun. 3, 1987, pp. 167-171.
"Magnetic and Eddy-Current Methods", Higher Technical Institute, 1984 Plenum Publishing Corp, pp. 399-409.
"Elements of Electricity", William H. Timbie, The Magnetic Circuit, Chap. 6, pp. 158-161, John Wiley & Sons, Inc., New York.

*Primary Examiner*—Gerard R. Strecker
*Attorney, Agent, or Firm*—Jeffers, Hoffman & Niewyk

[57] ABSTRACT

In a process and an apparatus for determining the coercive field strength and the maximum pitch of the hysteresis cure in set-up techniques a test body is magnetized in a magnetic field of an exciter coil fed with an alternating current, as the hysteresis curve of the test body is traversed a number of times with the frequency of the alternating current and the tangential field strength on the test body surface generated by the exciter coil is detected continuously with the aid of a magnetic field strength sensor during the traversing of the hysteresis curve. From a harmonic analysis of the time course of the tangential field strength within one period there is calculated a distortion factor for the determination of the maximum pitch of the hysteresis curve. The coercive field strength is ascertained by the means that the point of time of the first zero passage of the harmonic signal after the zero passage of the tangential field strength signal is sought and the amplitude of the tangential field strength signal present at this point of time is regarded as measure for the coercive field strength.

14 Claims, 3 Drawing Sheets

PROCESS AND APPARATUS FOR THE NONDESTRUCTIVE MEASURING OF MAGNETIC PROPERTIES OF A TEST BODY, BY DETECTING A TANGENTIAL MAGNETIC FIELD AND DERIVING HARMONIC COMPONENTS THEREOF

The invention relates to a process for the nondestructive measuring of magnetic properties of a test body which in set-up technique is magnetized in a magnetic field of an exciter coil fed with an alternating current, as the hysteresis curve of the test body is run derived several times with the frequency of the alternating current. The tangential field strength generated by the exciter coil on the test body surface is continuously detected with the aid of a magnetic field sensor during the traversing of the hysteresis curve, there being derived during the traversing of the hysteresis curve a signal whose variation with time is correlated with the variation with time of the tangential field strength i.e. the amplitude of the tangential component of the magnetic field which is parallel to the surface of the test body.

The invention relates likewise to an apparatus for the nondestructive measuring of magnetic properties of a test body with a magnetization yoke which may be placed on the test body to be investigated with its two magnetic poles. The exciter coil of the yoke is connected with a bipolar network apparatus for the traversing of the hysteresis curve of the test body and between the magnetic poles of which there is arranged a magnetic field strength sensor for the detection of the tangential field strength. The sensor is connected to a switching circuit which gives out the magnetic magnitudes determined by evaluating the variation with time of the tangential field strength.

Such an apparatus as well as a process of the type mentioned at the outset are known from DE-A1-30 37 932, in which in addition to the magnetic field strength sensor there is provided a second receiver for the detection of the Barkhausen noise or of the superheterodyne permeability of the test body during the traversing of the hysteresis curve. While the known apparatus equipped with an inductive receiver determines the coercive field strength of the investigated material by evaluating the noise maximum and determining the tangential field strength allocated to the noise maximum, the apparatus equipped with an eddy current coil determines the coercive field strength by means which measures the impedance of the eddy current coil dependent on the superheterodyne permeability of the investigated material. Further, the tangential field strength allocated to the maximum impedance is used for the determination of the coercive field strength.

Both the apparatus equipped with the inductive receiver for the determination of the Barkhausen noise and also the apparatus provided with the eddy current coil require, in addition of the magnetic field strength sensor, a senor for determining the magnitude of a second physical characteristic. Furthermore, by the use of the inductive receiver for the detection of the Barkhausen noise as well as of the eddy current coil for the detection of the superheterodyne permeability there are imposed restrictions in regard to the detectable measuring depth, which is especially disadvantageous when the hardening depth is to be determined, or for sorting of material wherein it is necessary to detect large volumes of material.

Proceeding from the above-mentioned state of the art, underlying the invention is the problem of creating a process and an apparatus which make it possible to detect magnetic properties, especially coercive field strengths, a well as the shape of the hysteresis curve at the coercive field strength point without using a sensor other than the magnetic field strength sensor also in the case of great measuring depths.

This problem is solved according to the invention in a process of the type mentioned at the outset by the means that the derived signal is determined from the variation with time of the tangential field strength signal, by means of a true-to-phase extremely narrow-band filtering, i.e. filtering which does not change the phase of the signal, from the periodic total signal of the tangential field strength. In this way the harmonic signal constituent is separated from the constituent of the fundamental wave signal, and through a linking of the harmonic wave signal with the total signal and/or the fundamental wave signal there are determined magnetic characteristic values of the test body.

In an apparatus according to the invention it is provided that the magnetic field strength sensor is connected to a true-to-phase narrow band filter i.e. a filter which does not change the phase of the signal, by which the time course of the periodic sensor signal is separable into its fundamental wave constituent and its harmonic constituent. The harmonic wave constituent together with the total signal of the sensor and/or the fundamental wave constituent feeds an evaluating processor for the calculation of the magnetic characteristic values of the test body.

Through the feature that for the determination of the magnetic characteristic values there is evaluated only the tangential field strength signal, the technical expenditure in apparatus is reduced by one measuring channel or a measuring branch, without its being necessary to dispense with the advantages of known processes and apparatuses. Underlying the invention is the insight that the measurement of only the tangential field strength permits the derivation of a measuring magnitude which linearly correlates with the coercive field strength. Moreover, the evaluation of the graph of the tangential field strength versus time makes possible the determination of a second measuring magnitude which stands in linear correlation to the maximum slope of the hysteresis curve.

In the following a preferred embodiment of the invention is explained in detail with the aid of the drawing.

Figure 2:
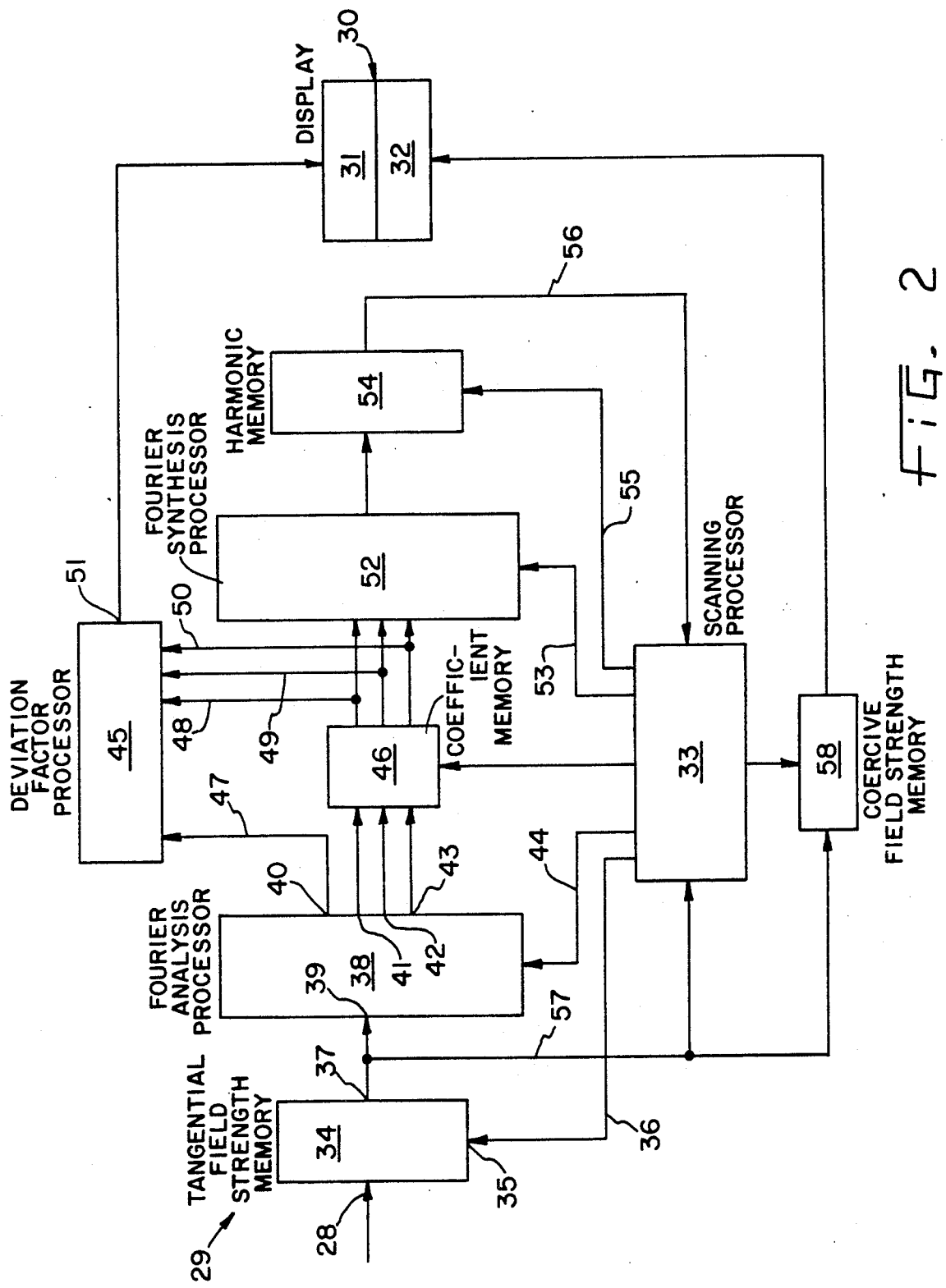
Figure 3:
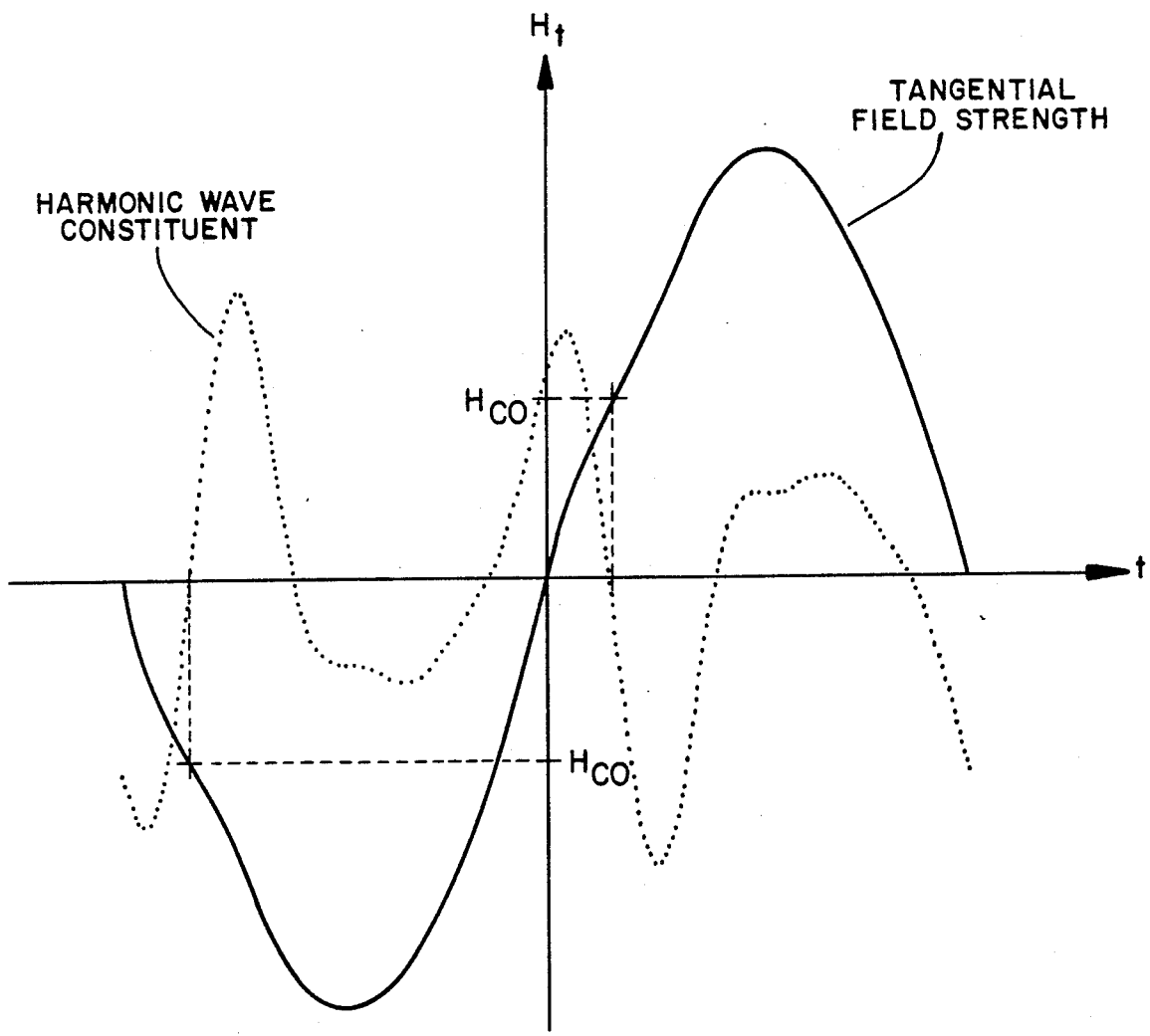

FIG. 1 shows a block circuit diagram of an apparatus according to the invention;

FIG. 2 the evaluating processor of the device according to the invention in a block circuit diagram and FIG. 3 the time variation graph of the tangential field strength detected by the magnetic field strength sensor in reference to the variation with time of the harmonic constituent contained therein for the illustration of the insight underlying the invention for the determination of the coercive field strength.

In FIG. 1 there is represented an example of execution for the apparatus for the nondestructive measuring of the coercive field amplitude as well as of the maximum slope of the BH curve or hysteresis curve. The apparatus has an oscillator 1, the frequency of which is tunable between 0 Hz and several kHz, in particular between 10 Hz and 100 Hz. In particular the oscillator 1, whose frequency and whose amplitude are selectable, can generate a sine signal of 50 Hz. Instead of the generation of a sine signal, however, it is also possible to provide an oscillator 1 which generates a periodic time signal of another form. The magnetization frequency, which in each case is selected to be between 0 Hz and several kHz, determines the measuring depth by virtue of the skin effect known to one skilled in the art.

The output 2 of the oscillator 1 is connected with the control input 3 of a bipolar network (mains) apparatus or of a bipolar power end stage i.e. an AC power supply 4. The output of the power end stage 4 feeds an exciter coil 5 which is wound on a set-up yoke 6 which consists, for example, of a large number of laminations or electro-plates stacked on one another. The set-up yoke 6 has two yoke shanks 7, 8 which may be placed for measuring the magnetic field on the surface 9 of a test body 10. In order to compensate for unevennesses and differing magnetic resistances which result, the amplitude of the oscillator 1 may be charged correspondingly, in order to achieve the result that the periodic alternating field generated by the set-up yoke 6 in the test body 10 remains constant in its magnetic field deviation.

Between the yoke shanks 7, 8 there is provided symmetrically to these a magnetic field strength sensor, especially a Hall probe 11, which likewise rests on the surface 9 and serves the purpose of detecting the tangential field strength on the upper side 9 of the test body 10.

The total inductance of the set-up yoke is dependent not only on the properties of the exciter coil 5 and the core material of the set-up yoke 6, but also on the magnetic properties of the test piece 10.

As is well known, in ferromagnetic materials the permeability is dependent on the magnetic field. This leads to a hysteresis influence and in the case of a sinusoidal exciter voltage on the exciter coil 5 to a non-sinusoidal time variation of the field strength in the test body 10. The hysteresis influence brings it about that besides the fundamental frequency also the odd-numbered higher harmonics or overwaves of the oscillator signal are excited. In consequence of the hysteresis influence there is yielded, therefore, a nonlinear frequency characteristic and therewith nonlinear distortions. The even-numbered harmonics are absent, because the hysteresis curve has a symmetrical course. The Hall probe 11 now makes it possible, in the case of an excitation with an oscillator 1, whose output voltage is sinusoidal to detect the course of the tangential field strength i.e. the component of the magnetic field which is parallel to the surface of the test body which deviates from the sine course. In FIG. 3 there is represented the non-sinusoidal course of the tangential field strength for one period.

The Hall probe 11 generates a periodic signal which with use of an oscillator 1 with a sinusoidal voltage has the form of a distorted sine wave. The output signal of the Hall probe 11 is amplified with the aid of an amplifier 12. The output of the amplifier 12 is connected, on the one hand, with the input 13 of an analog/digital converter 14 and, on the other hand, with a peak detector or maximum amplitude detector 15. Furthermore, the signal delivered by the amplifier 12 feeds a trigger circuit 16.

By the maximum amplitude detector 15 it is ascertained whether the signal fed to the analog/digital converter 14 is sufficiently great. If this is not the case, the amplitude of the oscillator 1 is readjusted and raised, which can be the case especially if by reason of unevenness an air gap exists between the yoke shanks 7, 8 and the surface 9 which leads to a poorer magnetic coupling and a higher magnetic resistance. The regulating circuit provided to stabilize the maximum amplitude contains, besides the amplifier 12 and the maximum amplitude detector 15, also a comparator circuit 17, which is connected with the output of the maximum amplitude detector 15. The comparator circuit 17 is connected, further, with a magnetic field deviation setting device 18, by which the maximum H-field deflection is adjustable. The output 19 of the comparator circuit 15 feeds the amplitude input 20 of the oscillator 1 for the delivery of a correction signal for the oscillator amplitude. The oscillator 1 has, further, a frequency input 21, which is connected with a frequency setting arrangement 22 for the adjustment and for the modification of the magnetization frequency. The above-described regulating circuit makes it possible to traverse the hysteresis curve of the test body 10 periodically and with a stabilized amplitude of the field strength.

In traversing the hysteresis curve of the test body 10 the output 23 of the analog/digital converter 14 delivers a digitalized tangential field strength signal. With the aid of a gate circuit 24 a period is cut out of the continuous tangential field strength signal. In FIG. 3 there is represented such a period of the tangential field strength, which can be detected, for example, by 1024 scanning points. The gate circuit 24 is opened with the aid of the trigger circuit 16 shortly before or from a zero passage for example one period of the tangential field strength signal. In FIG. 3 there is represented such a period of the tangential field strength, which can be detected, for example, by 1024 scanning points. The gate circuit 24 is opened with the aid of the trigger circuit 16 shortly before or from a zero passage for example one period of the tangential field strength signal. The requisite length for the time window of the gate circuit 24 can be determined by a threshold triggering or by an evaluation of the exciter frequency. In the circuit diagram presented in FIG. 1 the amplified tangential field strength signal presented on the input 25 of the trigger circuit 16 serves to adjust the opening time of the gate circuit 24 in dependence on the exciter frequency. Obviously it is also possible to connect the input 25 for this purpose directly with the output 2 of the oscillator 1. Each time when a period of the tangential field strength is to be detected, the control input 26 of the trigger circuit 16 is acted upon with a start signal. The starting signal can be generated, for example, by a start key 27 in an individual measurement or by a continuously occurring testing beat, if instead of a manual measuring release an automatic measuring release is desired.

From the above description it is yielded that after a single measuring release over the gate circuit 24 one period of the digitalized tangential field strength signal passes to the date input 28 of an evaluating processor 29 which handles the problems of the control of the apparatus, of the signal reception and of the signal processing.

The evaluating processor 29 determines from the form of the curve shown in FIG. 3 of the tangential field strength during one period the coercive field strength for the test body 10 as well as the maximum slope of the hysteresis curve and shows these values on a display unit 30 or passes these values over circuitry for the control of functions not represented in FIG. 1.

The evaluating processor 29 determines for the measuring volume established by the magnetizing frequency in the test body 10, the coercive field strength and the maximum slope of the hysteresis curve by an analysis of the deviation of the tangential field strength signal from the signal form on the output 2 of the oscillator 1, in which in the embodiment here described it is assumed that the oscillator 1 is a sine oscillator.

FIG. 2 shows an example of execution for the evaluating processor 29 together with the display unit 30 which presents a display field 31 for the maximum slope of the hysteresis curve and a display field 32 for the coercive field strength.

The evaluating processor 29 has a control and scanning processor 33 which controls, on the one hand, the various function blocks of the evaluating processor 29 and, on the other hand, serves for the scanning of the curve of the tangential field strength and of the harmonic constituent represented in FIG. 3.

The data input 28 is connected with a tangential field strength storer (memory unit) 34, which serves to store one period of the digitalized tangential field strength signal. The tangential field strength storer 34 has an address and control input 35 which is connected over an address and control line 36 with the control and scanning processor 33.

The output 37 of the tangential field strength storer 34 feeds the input 39 of a Fourier analysis processor 38 which performs a Fourier outgoing transformation of the tangential field strength signal. The tangential field strength measured by the Hall probe 11 is analyzed by the Fourier analysis processor 38 into its harmonic constituents, in which process on the output 40 there is provided the complex Fourier coefficient A1 of the fundamental wave and on the outputs, 41, 42 and 43 there are provided the complex Fourier coefficients A3, A5 and A7 of the respective higher harmonics or overwaves. The Fourier analysis processor 38, accordingly, resolves the total signal into a fundamental wave and three harmonics, where in consequence of the symmetry of the hysteresis curve there occur only harmonics of odd order and by evaluation of only three harmonics there is already possible a sufficiently high accuracy of measurement. Over a control line 44 the Fourier analysis processor 38 communicates with the control and scanning processor 33.

The evaluating processor 29 comprises a distortion factor processor 45 which contains circuits for the squaring, adding, dividing and root extraction as well as a calibrating storer (memory) with calibrating factors for various Hall probes 11 and set-up yokes 6. The distortion factor processor 45 obtains directly or on the roundabout way over a coefficient storer 46 as input values of the complex Fourier coefficients A1, A3, A5 and A7 over input lines 47 to 50. The distortion factor processor 45 calculates a distortion factor K as measuring magnitude from the Fourier coefficients in correspondence to the following formula $$K = \sqrt{\frac{|A3|^2 + |A5|^2 + |A7|^2}{|A1|^2}}$$

The distortion factor thus defined is a measuring magnitude that is smaller than 1 and which, as has been confirmed by tests, has a very high correlation with the maximum induced voltage in a coil embracing the test body 10. As compared to the process from the prior art comprehensive measuring technology, however, the apparatus described permits, in set up (emplacement) technique, measuring conveniently the maximum slope of the hysteresis curve. The distortion factor K is, accordingly, a measuring magnitude which presents after a multiplication with a calibrating factor, on the output 51 a measuring value for the maximum slope of the hysteresis curve or the differential permeability at the coercive field strength point. The maximum slope or the maximum steepness of the hysteresis curve is represented in the display field 31 of the display unit 30. Besides the evaluation of the proportionality of the distortion factor, the evaluating processor represented in FIG. 2 makes it possible, furthermore, in the manner described in the following, to determine the coercive field strength from the variation with time of the tangential field strength.

For this purpose, with utilization of the complex Fourier coefficients A3, A5 and A7 there is formed a harmonic signal which represents the harmonic constituent of the tangential field strength signal without the fundamental wave signal. In the hardware solution represented in FIG. 2, which can, of course, also be realized as a software solution on a multipurpose computer, the outputs of the coefficient storer 46 are connected with a corresponding number of inputs of a Fourier synthesis processor 52. The Fourier synthesis processor 52 makes it possible, from the complex Fourier coefficients A3, A5 and A7 by superposition at each time point to calculate the entire harmonic signal. This Fourier back-transformation after the filtering-out of the fundamental frequency occurs under the control of the control and scanning processor 33, which is connected with the Fourier synthesis processor 52 over a control line 53.

The harmonic signal delivered from the Fourier synthesis processor 52 presents in each case a time signal with the duration of one period of the fundamental signal or tangential field strength signal. A harmonic storer (memory) 54 connected with the output of the Fourier synthesis processor 52 stores one period of the harmonic signal, which is represented in FIG. 3 as the harmonic constituent of the tangential field strength.

The control and scanning processor 33 is connected over an address and control line 55 with the harmonic storer 54, so that the amplitude of the harmonic signal belonging to a particular scanning time point of the control and scanning processor 33 can be read out over a data line 56 from the harmonic storer 54. The control and scanning processor 33 is connected over a further data line 57 with the output 37 of the tangential field strength storer 54, in order through a linkage of the variation with time of the tangential field strength and of the harmonic constituent to derive a measuring magnitude $H_{CO}$ from the dependence of the tangential field strength $H_t$ on the time t. The measuring magnitude $H_{CO}$, derived in the following manner, is a measure for the coercive field strength $H_{CBH}$, which ordinarily is determined in comprehensive technology from the BH curve. Extensive tests have yielded a very high correlation between the measuring magnitude $H_{CO}$ and the coercive field strength $H_{CBH}$.

To derive the measuring magnitude $H_{CO}$ allocated to the coercive field strength, the control and scanning processor 33 compares the course of the tangential field strength represented for better understanding in FIG. 3 with the course of the harmonic constituent. There, the control and scanning processor 33 seeks the time point of the first zero passage of the harmonic signal or that of the harmonic constituent after a zero passage of the tangential field strength signal. The absolute tangential field strength value at the first zero place of the harmonic signal after the zero passage of the tangential field strength signal (remanence) is the measuring magnitude designated above with $H_{CO}$, which is proportional to the coercive field strength.

The above explanations show how with a harmonic analysis that was carried out with the aid of the Fourier transformation magnetic characteristic magnitudes can be determined. Experience has shown that the development of the tangential field strength into a Fourier eries up to the 7th harmonic is sufficient. The amplitudes of the higher harmonics determined from the Fourier coefficients lie in the range of the measuring accuracy of an analog/digital converter with a resolution of 10 bits.

To the control and scanning processor 33 there is allocated a coercive field strength storer (memory) 58 for the storing of the momentary amplitude of the tangential field strength at the time point of the first zero passage of the harmonic signal after the zero passage of the tangential field strength signal. The coercive field strength storer 58 is connected directly, therefore, with the output 37 of the tangential field strength storer 34. On output side the coercive field strength storer 58 communicates with the display field 32 of the display unit 30.

Besides the already mentioned possibilities of measuring the coercive field strength and the determination of a measuring magnitude correlating with the maximum slope of the hysteresis, the above described apparatus a well as the process discussed make it possible, further, to determine hardness profiles. For this it is merely necessary to carry out the measurement of the measuring magnitude $H_{CO}$ at different exciter frequencies. By a change of the exciter frequency with the aid of the frequency adjusting arrangement 22, by reason of the eddy current damping, different layer thicknesses in the test body 10 are analyzed. The depth range detectable in the measurement is restricted only by the penetration depth of the magnetic field generated by the set-up yoke 6. This is, for example, at 50 Hz according to the standard penetration depth formula about 4.4 mm. The use of exciter frequencies in the range of more than 1 Hz is especially of interest in view of the industrial suitability of the process described for material testing, since it allows correspondingly short measuring times and test beats. Although the Fourier transformation and the calculation to the total harmonic signal has been described on the basis of a hardware embodiment, it is obvious that this can also occur with software. The zero passage in the tangential field strength field gives in a software solution likewise the time trigger for the search of the following zero passage in the harmonic signal. The appertaining H-field value in the tangential field strength signal is then read out as $H_{CO}$.

It is also possible to carry out a splitting off of the harmonic signal from the tangential field strength signal in analog filter technique, which, however, leads to phase errors which render difficult the evaluation according to phase in the zero place search for the determination of the coercive field strength. The phase errors arising can, to be sure, be taken into account, which, however, in view of as variable as possible an exciter frequency represents a great expenditure, for which reason preferably, instead of an analog filter technique according to the embodiment described above, Fourier processors are used.

We claim:

1. A method for nondestructively measuring a magnetic property of a test body, said method comprising:
   magnetizing said test body by means of a magnetic field generated by an excitation coil which is energized with an alternating current, whereby a hysteresis curve of said test body is periodically and repeatedly traversed at the frequency of said alternating current and thereby generating a tangential magnetic field on a surface of said test body;
   detecting with a field strength sensor the periodic time varying strength of said tangential magnetic field and generating a tangential field strength signal;
   deriving a plurality of harmonic constituents from said tangential field strength signal by means of a filter and deriving from said harmonic constituents a periodic time varying harmonic constituent amplitude signal; and
   comparing the amplitudes of both said harmonic constituent amplitude signal and said tangential field strength signal as a function of time and deriving from said comparison the amplitude of a magnetic characteristic of said test body.

2. The method according to claim 1, wherein the filtering of the tangential field strength signal is accomplished by a Fourier analysis of one period of the tangential field strength signal, with the aid of which the complex amplitude coefficients of the fundamental wave constituent and of the harmonic constituents of said tangential field strength signal are determined to the harmonic of 7th order.

3. The method according to claim 2, wherein said distortion factor is derived from ratio of the geometric sum of the amplitudes of the harmonic constituents of the tangential field strength signal to the amplitude of the fundamental wave signal, said distortion factor comprising a measure of the slope of the hysteresis curve at the coercive field strength.

4. Method according to claim 2, wherein the amplitude of the tangential field strength signal at the point in time at which the amplitude of the harmonic constituent amplitude signal first reaches zero after the amplitude of the tangential field strength signal has passed through zero.

5. The method according to claim 1, wherein a distortion factor is derived from the ratio of the geometric sum of the amplitudes of the harmonic constituents contained in the tangential field strength signal to the amplitude of the fundamental wave signal, said distortion factor comprising a measure of the slope of the hysteresis curve at the coercive field strength.

6. The method according to claim 1, wherein the coercive field strength is determined to be the amplitude of the tangential field strength signal at the point in time at which the amplitude of the harmonic constituent amplitude signal first reaches zero after the amplitude of the tangential field strength signal passes through zero.

7. The method according to claim 6, wherein for the determination of hardness gradients and of the hardening depth the frequency of said alternating current is tuned through a range of values to magnetize the test body.

8. An apparatus for the nondestructive measuring of magnetic properties of a test body, said apparatus comprising:
- a set-up yoke including two magnetic poles adapted to be arranged on a surface of a test body;
- an exciter coil operatively associated with said yoke for generating a magnetic field in said test body;
- an alternating power supply connected to said coil;
- a magnetic field strength sensor arranged to generate a signal representative of the tangential magnetic field strength on a surface of said test body;
- circuit means connected to said sensor for providing the magnitude of said tangential field strength signal as a function of time;
- a filter connected to said switching circuit for deriving a plurality of harmonic constituents from said tangential field strength signal and for deriving a composite time varying harmonic constituent amplitude signal therefrom; and
- a processing circuit connected to said filter for calculating a magnetic characteristic of said test body from the harmonic constituent amplitude signal and said tangential field strength signal.

9. Apparatus according to claim 8, wherein the processing circuit comprises a distortion factor processor for determining a distortion factor from the amplitudes of said harmonic constituents and the amplitude of the fundamental component, said distortion factor providing the transfer interval between the exciter coil and the magnetic field strength sensor as a measure of the slope of the hysteresis curve and the coercive field strength.

10. Apparatus according to claim 9, wherein the filter comprises a Fourier analysis processor, said distortion factor processor connected to an output of said Fourier analysis processor, said Fourier analysis processor deriving from said tangential field strength signal the harmonic constituents up to the harmonic of the 7th order.

11. Apparatus according to claim 8, wherein said processing circuit comprises a scanning processor for scanning said tangential field strength signal and the harmonic constituent amplitude signal and for generating a selection signal to determine when the amplitude of the harmonic constituent amplitude signal first reaches zero after the amplitude of the tangential field strength signal passes through zero.

12. Apparatus according to claim 11, wherein said processing circuit comprises a Fourier analysis processor for the separation of said plurality of harmonic constituents and a Fourier synthesis processor for combining said harmonic constituents into said harmonic constituent amplitude signal.

13. Apparatus according to claim 8, wherein said processing circuit comprises a Fourier analysis processor for the separation of said plurality of harmonic constituents and a Fourier synthesis processor for combining said harmonic constituents into said harmonic constituent amplitude signal.

14. Apparatus according to claim 13, wherein the amplitudes of the 3rd, 5th and 7th order of harmonic constituents may be combined by the Fourier analysis processor and the Fourier synthesis processor.

* * * * *